(12) United States Patent
Fisher et al.

(10) Patent No.: US 9,164,299 B2
(45) Date of Patent: Oct. 20, 2015

(54) OPHTHALMIC LENS DISPENSING METHOD AND SYSTEM

(75) Inventors: Scott Warren Fisher, Flagstaff Hill (AU); Philip Charles Lachlan Stephenson, Meadows (AU); Kym Ansley Stockman, Happy Valley (AU)

(73) Assignee: CARL ZEISS VISION AUSTRALIA HOLDINGS LIMITED, Lonsdale, South Australia (AU)

( * ) Notice: Subject to any disclaimer, the term of this patent is extended or adjusted under 35 U.S.C. 154(b) by 292 days.

(21) Appl. No.: 12/447,187

(22) PCT Filed: Oct. 26, 2007

(86) PCT No.: PCT/AU2007/001636
§ 371 (c)(1),
(2), (4) Date: Jul. 15, 2009

(87) PCT Pub. No.: WO2008/049173
PCT Pub. Date: May 2, 2008

(65) Prior Publication Data
US 2010/0026955 A1  Feb. 4, 2010

(30) Foreign Application Priority Data
Oct. 26, 2006  (AU) .................................. 2006905950

(51) Int. Cl.
*G02C 7/02* (2006.01)
*A61B 3/00* (2006.01)
*G02C 13/00* (2006.01)
*A61B 5/00* (2006.01)

(52) U.S. Cl.
CPC ............. *G02C 13/003* (2013.01); *A61B 5/0064* (2013.01)

(58) Field of Classification Search
CPC ........... B24B 49/02; G02C 1/06; G02C 5/008
USPC ............ 351/41, 159, 161, 169, 176, 177, 178
See application file for complete search history.

(56) References Cited

U.S. PATENT DOCUMENTS 4,852,184 A    7/1989  Tamura et al.
5,576,778 A   11/1996  Fujie et al.
(Continued)

FOREIGN PATENT DOCUMENTS

DE      42 24 922 A1   2/1994
EP      0 446 698 A2   9/1991
(Continued)

OTHER PUBLICATIONS

PCT/ISA/210 dated Dec. 18, 2007.
(Continued)

*Primary Examiner* — Mahidere Sahle
(74) *Attorney, Agent, or Firm* — Buchanan Ingersoll & Rooney PC

(57) ABSTRACT

A method (100) of dispensing an ophthalmic lens for a wearer is disclosed. The method (100) includes measuring (104) the relative location of, and/or relationship between, selected anatomical features of a wearer's head or face to obtain one or more measurement values and processing (106) the one or more measurement values to design and/or select an ophthalmic lens having a shape that depends on the measured values. The ophthalmic lens element is then dispensed to the wearer. A dispensing system (200) is also disclosed.

32 Claims, 7 Drawing Sheets

(56) References Cited

U.S. PATENT DOCUMENTS

| | | |
|---|---|---|
| 5,983,201 A | 11/1999 | Fay |
| 6,095,650 A | 8/2000 | Gao et al. |
| 6,142,628 A | 11/2000 | Saigo |
| 6,231,188 B1 | 5/2001 | Gao et al. |
| 6,505,930 B1 | 1/2003 | Perrott et al. |
| 6,508,553 B2 | 1/2003 | Gao et al. |
| 6,634,754 B2 | 10/2003 | Fukuma et al. |
| 6,786,595 B1 * | 9/2004 | Thieberger .................... 351/159 |
| 6,944,327 B1 * | 9/2005 | Soatto ........................... 382/154 |
| 2001/0022649 A1 | 9/2001 | Fukuma et al. |
| 2003/0123026 A1 | 7/2003 | Abitbol et al. |
| 2005/0225719 A1 | 10/2005 | Kamishita et al. |

FOREIGN PATENT DOCUMENTS

| | | |
|---|---|---|
| EP | 1 136 869 A1 | 9/2001 |
| FR | 2 885 231 A1 | 11/2006 |
| JP | 2006-113425 A | 4/2006 |
| WO | WO 00/16683 | 3/2000 |
| WO | WO 00/23021 A1 | 4/2000 |
| WO | WO 01/23908 A1 | 4/2001 |
| WO | WO 01/32074 A1 | 5/2001 |
| WO | WO 01/79918 A1 | 10/2001 |

OTHER PUBLICATIONS

French Search Report dated Nov. 29, 2005 with English translation of search report categories.

Supplementary European Search Report issued on Mar. 4, 2011, by the European Patent Office in corresponding European Patent Application No. 07815440.8-2217. (3 pages).

Office Action (First Examination Report) issued on Mar. 11, 2011, by the European Patent Office in corresponding European Patent Application No. 07815440.8-2217. (6 pages).

Office Action (Patent Examination Report No. 2) issued on Jan. 9, 2013, by the Australian Patent Office in corresponding Australian Patent Application No. 2007308758. (6 pages).

* cited by examiner

OPHTHALMIC LENS DISPENSING METHOD AND SYSTEM

This application claims priority from Australian Provisional Patent Application No. 2006905950 filed on 26 Oct. 2006, the contents of which are to be taken as incorporated herein by this reference.

FIELD OF THE INVENTION

The invention broadly relates to methods and systems for dispensing ophthalmic lenses.

BACKGROUND TO THE INVENTION

Spectacle wearers are becoming increasingly discerning when selecting spectacles, such as sunglasses or prescription spectacles. Indeed, the 'look' of the spectacles, especially in terms of the look on the wearers face, can be the single most important determinative factor in a wearer's purchasing decision.

A significant factor in determining the look of the spectacles on the wearer's face is the extent to which the spectacles properly fit the wearer's head or face. Properly fitted spectacles will generally look more aesthetically pleasing than ones which fit poorly.

Spectacles typically consist of a frame and a set of ophthalmic lenses that are fitted to the frame. Although the shape of the frame and the ophthalmic lenses contributes to overall appearance of the spectacles, in conventional spectacle dispensing the shape of the frame is usually the focus of the dispensing process. Typically, a frame is selected first, and ophthalmic lenses are subsequently selected that fit the frame. For example, if a wearer requires a highly curve lens (such as a "wrapped" style lens), then a wrapped style frame is specified, and lenses are then selected that "best fit" the specified frame. Various frames will be tried until the best fit or match to expectations is achieved.

Thus, dispensing an ophthalmic lens for a wearer occurs somewhat incidentally and typically involves a trial and error process in which a wearer tries on several sets of frames, each of which is usually fitted with dummy lenses, until a set is selected that provides satisfactory aesthetics as well as, perhaps, a desired functional characteristics. Again, such a process typically involves a wearer selecting a particular frame, or style of frame, from a range of frame designs or styles, and then selecting an ophthalmic lens that fits the selected frame so as to provide a desired lens and frame combination.

Unfortunately, in conventional dispensing processes, the range of frame shapes available for selection is limited and, consequently, so is the range of ophthalmic lenses available for dispensing. Thus, even after an exhaustive trial and error process the selected ophthalmic lens may not properly fit the wearer's head or face and thus may also not provide an aesthetic appearance that meets the wearer's aesthetic requirements or taste. In other words, a wearer may have no choice but to settle for an ophthalmic lens having a shape that does not completely satisfy their aesthetic or functional requirements.

SUMMARY OF THE INVENTION

The present invention provides a method of dispensing an ophthalmic lens for a wearer, the method including measuring the relative location of, and/or the relationship between, selected anatomical features of a wearer's head or face to obtain one or more measurement values; processing the one or more measurement values to design and/or select an ophthalmic lens having a shape that depends on the measured values; and dispensing the ophthalmic lens to the wearer.

Preferably, the shape of the ophthalmic lens that depends on the one or more measured values includes a surface shape of the ophthalmic lens. The surface shape may include the shape of the front surface (that is the object side) of ophthalmic lens or the shape of the back surface (that is, the ocular side) of the ophthalmic lens. However, it is to be appreciated that the shape need not be restricted to a surface shape, and thus the shape may also include a shape associated with another characteristic of the lens, such as, for example, the shape of the perimeter of the ophthalmic lens.

The present invention also provides a system for selecting and/or designing an ophthalmic lens for dispensing to a wearer, the system including a measuring apparatus for measuring the relative location of, and/or the relationship between, selected anatomical features of a wearer's head or face to obtain one or more measurement values; and a processing device for processing the one or more measurement values to design and/or select, for dispensing, an ophthalmic lens having a shape that depends on the one or more measurement values.

The present invention also provides a programmed computer for selecting and/or designing an ophthalmic lens for dispensing to a wearer, the computer including a processing device; a memory; a set of program instructions resident in the memory and executable by the processor to accept one or more measurement values expressing the relative location of, and/or the relationship between, selected anatomical features of a wearer's head or face and process the measurement values to dispense an ophthalmic lens having a shape that depends on the measured values.

The present invention also provides an integrated scanning and processing system for selecting and/or designing an ophthalmic lens for dispensing to a wearer, the system including: a scanning device for scanning the wearer's head or face to provide three-dimensional scan data; an input device for inputting or selecting selected anatomical features of the wearer's face or head; and a processing device for obtaining, from the three-dimensional scan data, one or more measurement values expressing the relative location of, and/or the relationship between, of the anatomical features and processing the one or more values to design and/or select, for dispensing, an ophthalmic lens having a shape that depends on the one or more measured values.

The present invention also provides a computer readable media storing a set of program instructions that are executable by a computer processor to accept one or more measurement values expressing the relative location of, and/or the relationship between, selected anatomical features of a wearer's head or face; and process the one or more measurement values to select and/or design, for dispensing, an ophthalmic lens having a shape that depends on the measured values.

The present invention also provides an ophthalmic lens that has been selected and/or designed for dispensing to a wearer by a method that includes measuring the relative location of, and/or the relationship between, of selected anatomical features of a wearer's head or face to obtain one or more measurement values; and processing the one or more measurement values to design and/or select, for dispensing, an ophthalmic lens having a shape that depends on the one or more measured values.

A particular advantage of the present invention is that it provides an ophthalmic lens that substantially conforms to contours of head or facial features of the wearer.

The present invention may have a variety of applications, ranging from dispensing ophthalmic lenses including a front surface having a single base curve selected on the basis of the measured values, through to the dispensing of lenses having complex shapes that match a wearer's facial contours and that may also provide optimal protection/coverage for a particular function or application.

The present invention thus provides an ophthalmic lens having a shape that depends on measurement values for the relative location of, and/or the relationship between, selected anatomical features of a wearer's head and/or face.

An ophthalmic lens dispensed by an embodiment of the present invention may be manufactured using free-form cutting or other manufacturing technology to cut an ophthalmic lens, such as a wrap lens, that matches, at least to an extent, the shape of the wearer's face. In addition, the optics of the lens may be corrected to take into account the front and back surface shapes, wrap angles, vertex and task application. For example, an ophthalmic lens in accordance with an embodiment of the present invention may include a front and/or back surface that provides a surface shape that conforms to desired ergonomic and face shape constraints as well as optical compensations on either the front surface, the back surface or both surfaces.

In one embodiment, the front surface provides a surface shape that depends on the measurement values for the relative location of, and/or the relationship between, selected anatomical features of a wearer's head and/or face, and the back surface includes a central zone having a surface shape that provides an optical compensation for substantially removing optical aberrations introduced by the shape of the front surface. For example, the central zone may be shaped so that optical aberrations introduced by the shape of the front surface are substantially removed so that a desired optical prescription (Rx) is maintained for viewing through the central zone.

Preferably, the central zone provides a clear optical zone for at least the wearer's typical central visual field. In this respect, the wearer's typical central visual field is the extent of the area visible to the wearer's eye when the eye is fixating straight ahead. As will be appreciated, the central zone may provide a clear optical zone that is larger than the wearer's typical central visual field and may be sized to provide a clear optical zone for an extended visual field corresponding with the area visible to the wearer's eye for a range of eye rotations.

It is also envisaged that characteristics of the shape, such as changes in curvature, may be located at a transition point between the optical zone and a cosmetic zone that curves around the wearers face.

The dispensing method mentioned above may include dispensing an ophthalmic lens that has been selected from a group of known ophthalmic lens designs. For example, an embodiment of the present invention may be used on-site by a dispenser to provide a recommendation for the selection of a suitable lens design from a group of known lens designs, preferably in a reasonably short period of time.

Alternatively, the dispensing may include designing a custom ophthalmic lens design, and the subsequent manufacture of a custom ophthalmic lens suitable for the wearer. In such an embodiment, the generation of such a custom ophthalmic lens design will utilise, during the processing step, the one or more measurement values expressing the relative location of, and/ or relationship between, the selected anatomical features so that the shape of the custom ophthalmic lens design is influenced by, and thus depends on, those one or more measurement values.

The measurement values for the selected anatomical features of the wearer's head or face may be used to generate a profile that approximates a contour mapping at least a frontal aspect of the wearer's head or face. The contour may include, for example, a contour that lies in a substantially horizontal plane, such as a horizontal plane that intersects the selected anatomical features, in which case the selected anatomical features may be located either side of the wearer's eye so as to include, for example, a nasal-side anatomical feature and a temporal-side anatomical feature. Alternatively, the contour may lie in a substantially vertical plane that intersects the selected anatomical features, in which case the selected anatomical features may be located above and below the wearer's eye so as to include, for example, an upper anatomical feature and a lower anatomical feature, relative to the wearer's eye.

Measuring the relative location of, and/or relationship between, selected anatomical features may be performed by any suitable method. The actual measurement method may vary depending on the anatomical features being measured.

In an embodiment, the relative location of, and/or relationship between, the selected anatomical features may be measured using a mechanical measurement device such as a ruler, a protractor or a goniometer. However, in another embodiment, the relative location and/or relationship of the selected anatomical features may be measured using a three-dimensional (3D) volumetric scanning system that provides three-dimensional scan data for the wearer's face and head. A suitable 3D volumetric scanning system may include a laser scanning system or a system that uses structured light techniques.

Irrespective of whether the relative location of, and/or relationship between, the selected anatomical features is measured using a mechanical measurement device, or a 3D volumetric scanning system, the resultant measurement data is processed to obtain one or more measurement values expressing the relative location and/or relationship of each of the selected anatomical features. As will be appreciated, the type of processing, at least in terms of its complexity, will vary according to the measurement method. For example, where the relative location and/or relationship between the selected anatomical features is measured using a mechanical measurement device, the processing may involve indexing the measurement values into a look-up table to select an ophthalmic lens having a surface shape that is matched to the one or more measured values, or a range of measurement values within which the actual one or more measurement values fall. On the other hand, where the relative location, and/or relationship between, the selected anatomical features is measured using a 3D scanning system, the processing may be performed by suitable computer software that includes algorithms for extracting the measurement values from the 3D scan data and curve-fitting algorithms for a deriving a suitable shape, such as a suitable surface shape, based on the one or more measurement values.

The anatomical features of the wearer's face and/or head may include, for example, the location of the wearer's nose, anatomical surface features of the wearer's eye(s) and/or eyelid(s), the side of the head, or an angle between the front plane and a side plane of the wearer's head. In terms of suitable anatomical features of the head, they may include one or more of the zygion, the zygomatic arch, frontal eminence, the temporomandibular joint and the mandible angle. Suitable anatomical surface features of the eye and/or eyelids may include one or more of the pupil, the medial angle, the lateral angle, the medial commissure, the lateral commissure, the medial canthus, the lateral canthus, the lacarimal caruncle, the nasojugal fold, the lower eyelid margin, and the palperal fissure.

Ideally, the selected anatomical features will be suitable for generating a profile approximating plural contours of at least a frontal aspect of the wearer's face and/or head and, consequently, for deriving a three-dimensional surface shape for the ophthalmic lens. In this respect, when we say that the shape of the ophthalmic lens depends on the measurement values expressing the relative location of, and/or the relationship between, the selected anatomical features, we mean that a characteristic of the shape of the lens is determined or derived from those values. Again, that characteristic may be a two-dimensional or a three-dimensional characteristic of the surface shape.

By way of example, measurement of the relative location of, and/or relationship between, the selected anatomical features may provide information about the size of the ophthalmic lens' central zone (that is, the zone to be placed 'in front' of the wearer's eye) and the position of the 'turnaround' point of the lens' surface in order for the surface to fit along the side of the head.

Ideally, the dispensed ophthalmic lens will have a surface shape that provides an aesthetically pleasing lens product, based on the broad idea that an aesthetically pleasing product is one having a shape that conforms to the general contours of the wearer's face and head. As outlined above, in order to achieve that, specific anatomical features on the head or face are selected, and their relative position and relationship to each other measured. These points on the head or face can then be matched to appropriate features of the shape of the lens.

In another embodiment, the shape of the dispensed ophthalmic lens may also depend on other values or factors. For example, the shape may also depend on values that express, or that relate to, a wearer's functional requirements of the ophthalmic lens, such as an intended use, task or application. Therefore, not only would the method of the present invention find use for the dispensing of ophthalmic lenses that provide an improved facial fit, but also in areas for the development of lens designs that cater for different wearer requirements, particularly in terms of their functional requirements, such as may be required for sporting, recreational or occupational pursuits.

A wearer's functional requirements will preferably include requirements that relate to an intended application of the ophthalmic lenses and will typically depend on an intended use, task or application of the ophthalmic lenses. For example, if the wearer intends to wear ophthalmic lenses during an activity such as cycling, the functional requirement may include a requirement that the ophthalmic lenses provide a low value of aerodynamic coefficient of drag. Thus, in an example application of a method embodiment a cyclist may sit on a bicycle in a racing position, such as an aerodynamic position, specific helmet and then be scanned/measured to obtain one or more measurement values expressing the location of, or relationship between, selected anatomical features of the wearer's head or face, which are then processed, in conjunction with one or more measurement values for the helmet, to provide a lens shape that is designed to minimise drag in conjunction with the position, preferred posture and helmet. The rear surface of the ophthalmic lens is then designed to correct for the distortions introduced by the aerodynamic demands of the front surface.

Similarly, if the wearer intends to use ophthalmic lenses during an activity such as water skiing, the functional requirement may be a requirement that the ophthalmic lens provide protection from splash. In this respect, an ophthalmic lens that provides splash protection may have a surface shape that is configured to fit closely around the eye orbit and side of the face to preclude, or at least reduce, splashes from entering the eye from behind the lens.

Similarly, a lens may be designed to allow full rotation of the eye in any direction without the wearer being able to see the edge of the lens or any containing frame.

Each functional requirement may be specified precisely or generally. For example, a functional requirement may be specified precisely as a numerical value for a requirement parameter (such as, for example, a numerical value for a coefficient of drag); or generally by specifying an acceptable range of numerical values within which a value of a requirement parameter may fall, an acceptable category from a range of different categories (for example, racing, training, practising), or an acceptable level from a range of levels (for example, low, medium, high).

In one embodiment, the functional requirements dictate the selection of the anatomical features for which measured values are obtained and processed. For example, in one embodiment, the surface shape of the lens may be dictated by the relative location of, and/or the relationship between, anatomical features that correlate with a given functional requirement, or functional requirements.

It is to be appreciated that the above described examples of functional requirements, and the specification of those requirements, should not be construed as limiting the scope of the present invention. In this respect, the above examples are merely intended to assist the reader in understanding of the application of the present invention. It will be appreciated that other functional requirements, and other ways of specifying those requirements, may be applicable. Indeed, it is anticipated that any functional requirement which can be addressed by varying the surface shape of an ophthalmic lens may be applicable. In this respect, further non-limiting examples include glare protection requirements and field of view requirements.

BRIEF DESCRIPTION OF DRAWINGS

The invention will now be described in further detail by reference to the attached drawings illustrating example forms of the invention. It is to be understood that the particularity of the drawings does not supersede the generality of the invention.

In the drawings.

DETAILED DESCRIPTION OF DRAWINGS

Various terms that will be used throughout the specification have meanings that will be well understood by a skilled addressee. However, for ease of reference, some of these terms will now be defined.

The term 'ophthalmic lens', and variations thereof, as used throughout the specification is to be understood to mean any lens of an optical quality transparent material intended to be supported by the wearer's head or face. Thus, the term can refer to reading glasses, non-prescription sun glasses, safety glasses, glasses for sporting application, driving glasses and the like.

The term 'relative location', when used in relation to the location of selected anatomical features of the wearer's head or face is to be understood to be a reference to the location of a selected anatomical feature with respect to a reference point or datum. A measurement value expressing the relative location of a selected anatomical feature may be expressed as a co-ordinate of a co-ordinate system such as a two-dimensional co-ordinate system or a three-dimensional co-ordinate system. Alternatively, the relative location may be expressed using a polar or rectangular co-ordinate system. The reference point may be the location of another selected anatomical feature or it may be defined in some other way.

The term 'relative relationship', when used in relation to the relationship between selected anatomical features of the wearer's head or face is to be understood to be a reference to a geometric relationship between selected anatomical features. A measurement value expressing the relative relationship between selected anatomical features may be expressed as an angle or a displacement, such as a length, a depth or a height.

Figure 1:
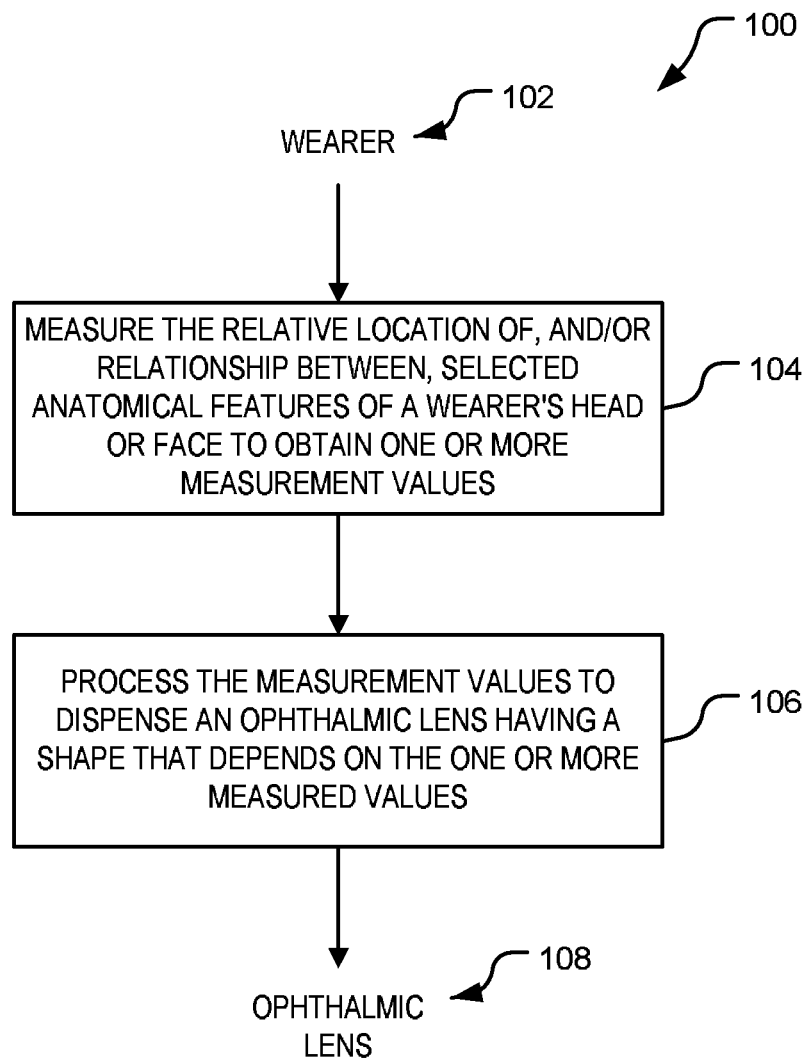
FIG. 1 is a simplified flow diagram for a method embodiment of the present invention.

FIG. 1 depicts a flow diagram for a method 100 according to an embodiment of the present invention. As shown, the method 100 includes measuring 104 the relative location of, and/or relationship between, selected anatomical features of a wearer's head and/or face to obtain one or more measurement values, and processing 104 the one or more measurement values to design and/or select, for dispensing, an ophthalmic lens 108 having a shape that depends on the one or more measured values. Ideally, the shape of the dispensed ophthalmic lens 106 includes a surface shape that conforms to the general contours of a wearer's face.

The dispensing of an ophthalmic lens 106 in accordance with a method embodiment of the present invention may include selecting, based on the processing 104 of the one or more measurement values, an ophthalmic lens 108 having a single base curve that blends in with the facial features of the wearer 102 or, alternatively, a more complex surface shape that conforms with a wearer's 102 head or facial features. For example, an ophthalmic lens 106 may provide a surface shape that conforms to the 'natural' curve from the bridge of the wearer's nose (or medial angle) to the temporomandibular joint or ear or include an even more complex form with application specific goals in mind.

Figure 2:
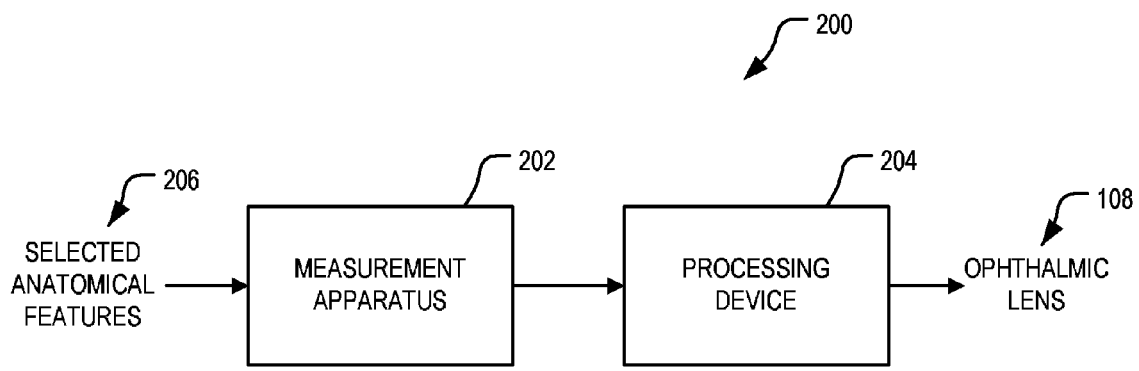
FIG. 2 is a block diagram for a system in accordance with an embodiment of the present invention.

FIG. 2 depicts a block diagram for a system 200 in accordance with an embodiment of the present invention. The system 200 includes a measurement apparatus 202 and a processing device 204. The measuring apparatus 202 is operable to measure the relative location of, and/or relationship between selected anatomical features 206 of a wearer's head or face to obtain one or more measurement values.

The processing device 204 processes the one or more measurement values to dispense the ophthalmic lens 108. The processing device 204 may include, for example, a personal computer (such as a desktop computer), or a hand-held computer (such as a personal digital assistant), or a laptop computer programmed with suitable software.

Figure 3:
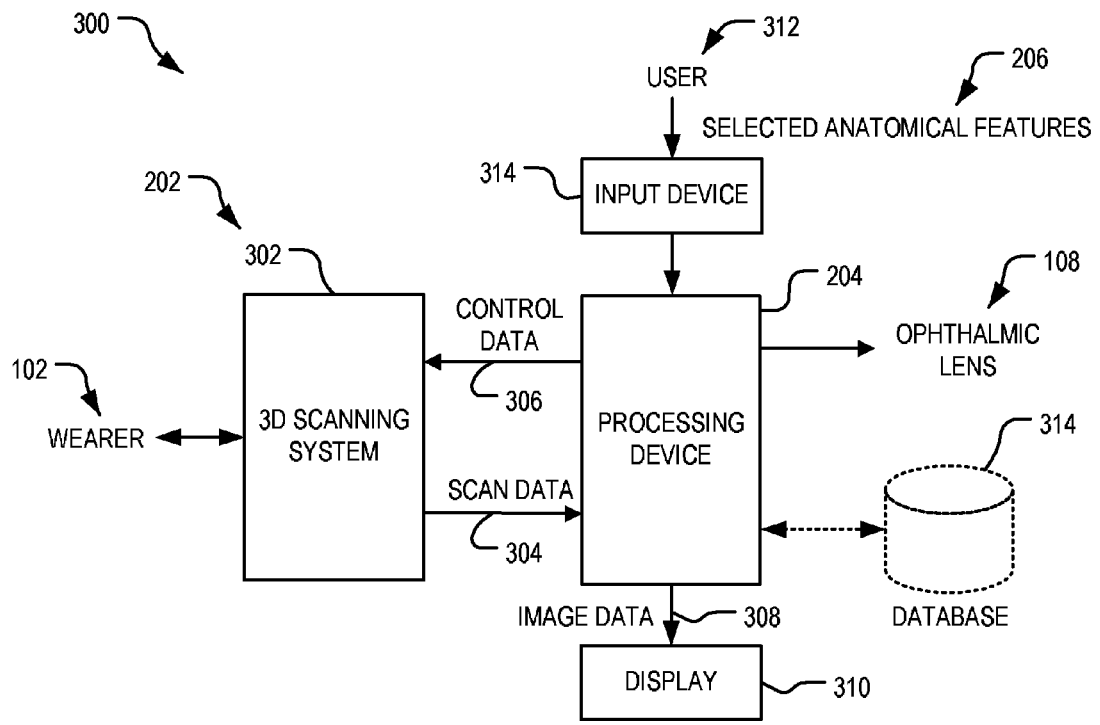
FIG. 3 is a block diagram for a system in accordance with a second embodiment of the present invention.

FIG. 3 depicts a second embodiment of a system 300 in accordance with the present invention. The system 300 depicted in FIG. 3 includes a measurement apparatus 202 in the form of a 3D volumetric scanning system 302, such as a Polyhemus FastSCAN scanner, that is operable to scan a wearer's head or face so as to provide 3D scan data. As is shown, the volumetric scanning system 302 is interfaced to the processing device 204 to permit data communication therebetween.

Figure 4:
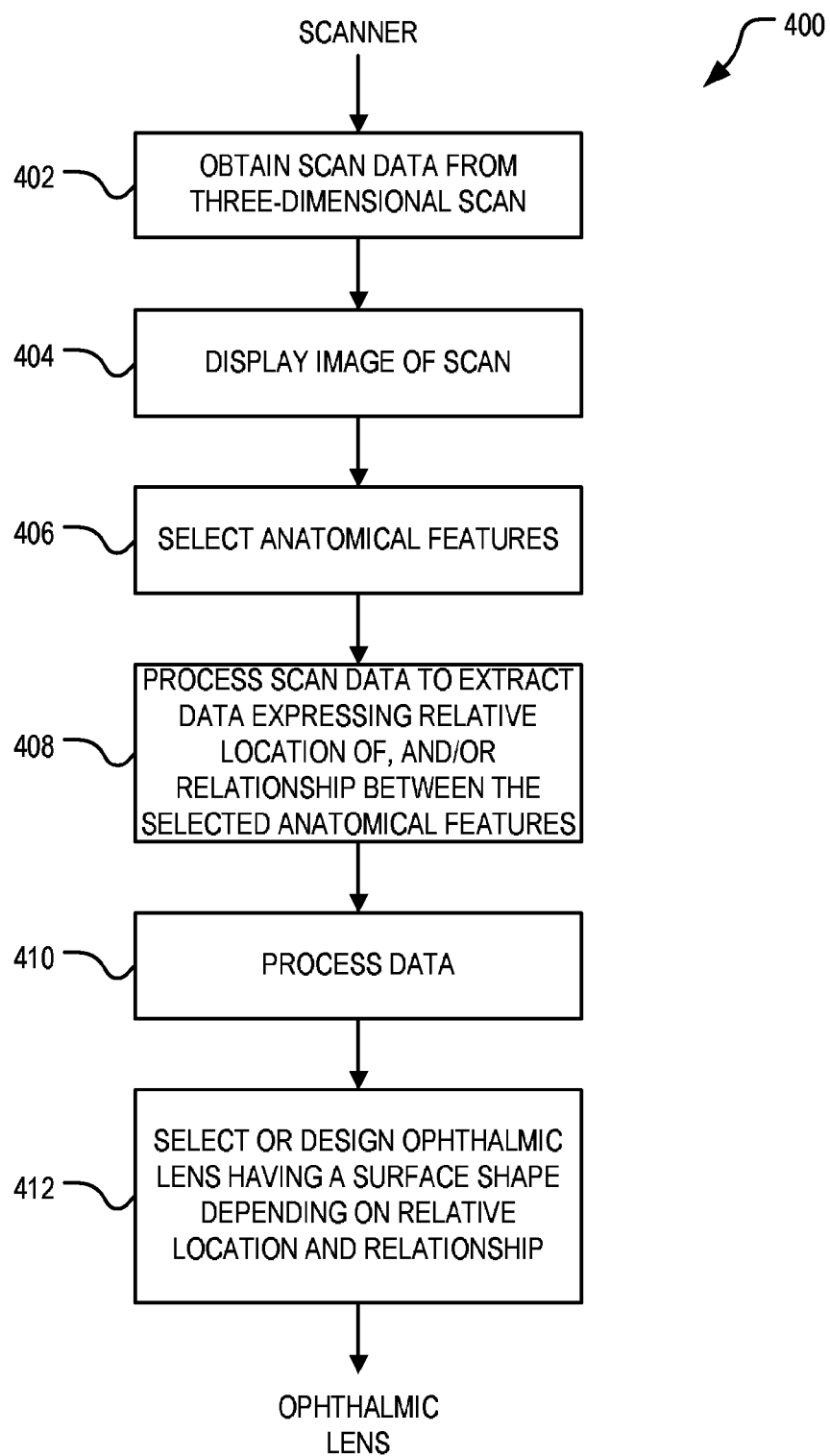
FIG. 4 is a flow diagram for a method embodiment applicable to the system depicted in FIG. 3.

In the embodiment illustrated in FIG. 3, and with reference also to the flow diagram shown in FIG. 4, the processing device 204 obtains 402 (ref. FIG. 4) scan data 304 from the scanning system 302 under the control of the processing device 204, as determined by control data 306. The control data 306 includes data that configures and controls the operation of the 3D scanner 302.

Figure 5:
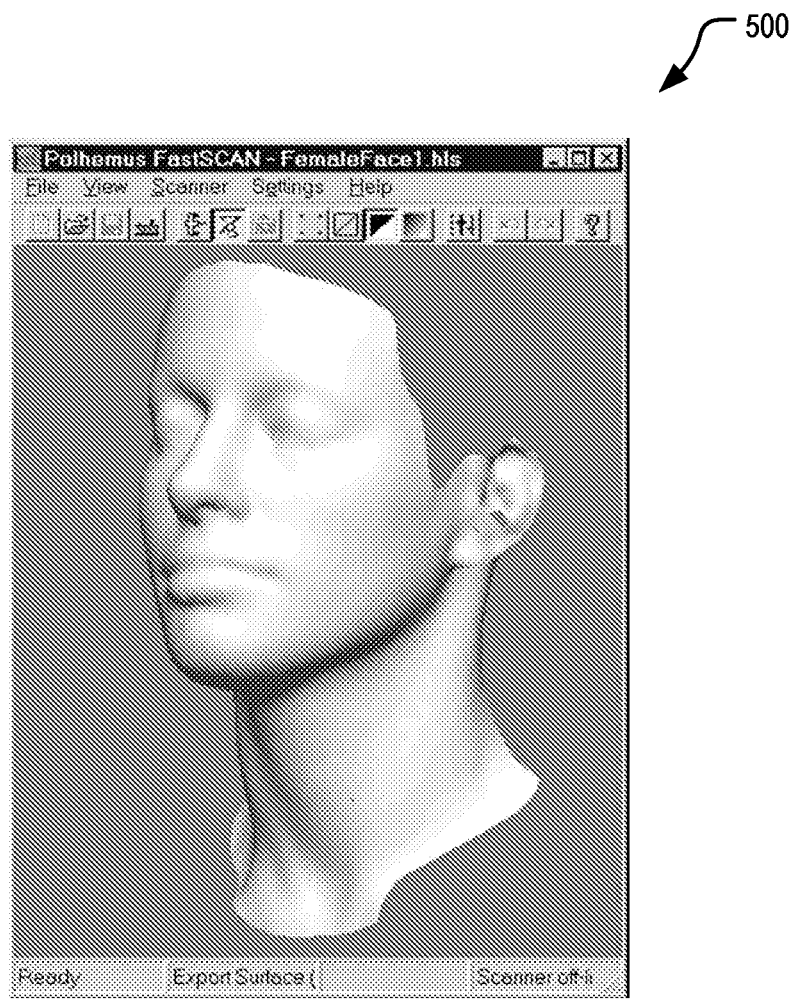
FIG. 5 is an example of an image displaying scan data.

Having obtained the scan data 304, the processing device 204 then generates image data 308 for display 404 (ref. FIG. 4) on display 310. The display provides a graphical image representing the scanned data and may be, for example, an image 500 similar to that depicted in FIG. 5.

A user 312, such as a dispenser, then operates the input device 314, such as a mouse, a keyboard a trackball or the like, to enter select anatomical features 206 of the wearer's head or face. The entering of the select anatomical features 206 may include, for example, selecting anatomical features from a list of anatomical features, or interacting with the displayed image so as to designate anatomical features on the displayed image.

Having selected the anatomical features of the wearer's head or face, the processing device 204 then processes the scan data 304 to extract one or more measurement values expressing the relative location of, and/or relationship between, the selected anatomical features. In this case, the extracted values are then processed at step 410 (ref. FIG. 4) by the processing device 204 to select or design, at step 412 (ref FIG. 4) an ophthalmic lens having a surface shape that depends on the relative location of, and/or the relationship between, the selected anatomical features. As shown, the system 300 optionally includes, or is able to access, a database 314 (shown dashed) containing data for a group of ophthalmic lens designs from which a suitable lens design is selected on the basis of the processing of the one or more measured values.

Example 1

Figure 6A:
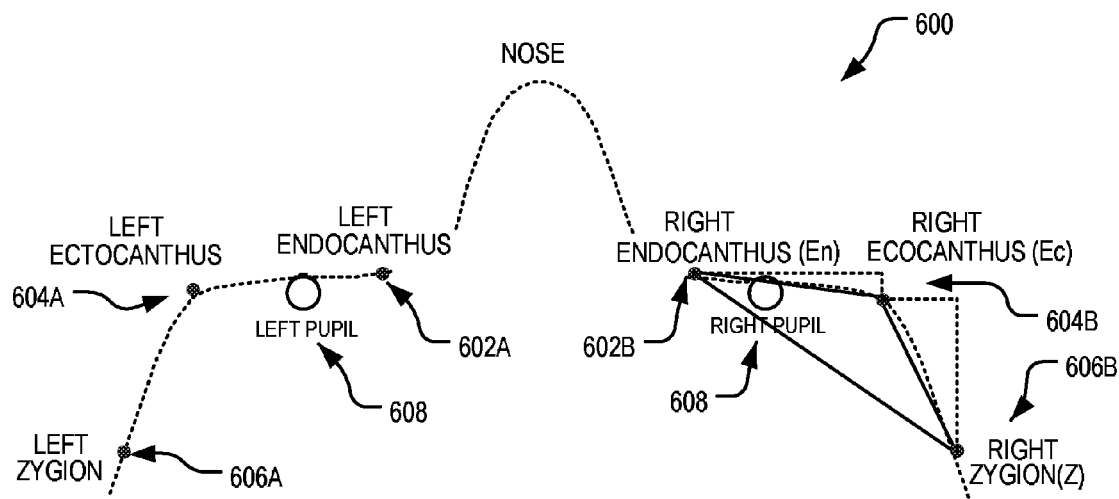
FIG. 6A is a face profile including examples of anatomical features.

With reference to FIG. 6A, from a 3D image of a face/head scan the position of the following anatomical features are measured:

1. Left and right endocanthus (602A, 602B), that is, the inner corner of the eye where the upper and lower lids meet;
2. Left and right ectocanthus (604A, 604B), that is, the outer corner of the eye where the upper and lower lids originate; and
3. Left and right zygion (606A, 606B), that is, the most lateral point on the side of the zygomatic arch.

In this example, the location of the points 602A and 604A, and 602B and 604B respectively determines the position of the lens' central zone to be placed in front of the wearer's eye. On the other hand, the location of points 604A and 606A, and 604B and 606B respectively determines the position of the 'turnaround' point of the lens' surface in order for the surface to fit along the side of the head.

Figure 6B:
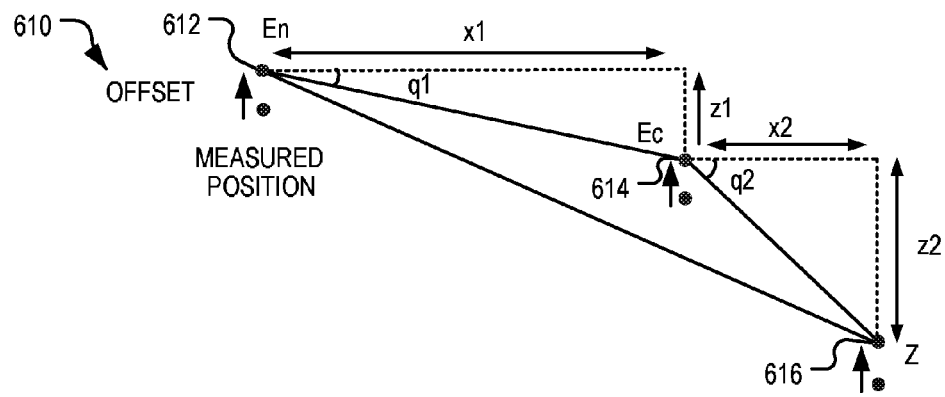
FIG. 6B is a diagram depicting an example of measured relative location and/or relationship values for the anatomical features depicted in FIG. 6A.

With reference to FIG. 6B, a pre-determined offset distance 610 is then applied to the measured values to allow for the ophthalmic lens to have clearance from the face/eyelashes.

The offset distance 610 will depend on the application of the lenses. For example, an ophthalmic lens that is to be used for protection may sit closer to the face and, hence, the offset distance 610 may be less than for a lens that is purely designed for fashion or aesthetic purposes.

From the positions of the three offset points 612, 614, 616 the lengths x1, x2, z1 and z2 are calculated.

Figure 6C:
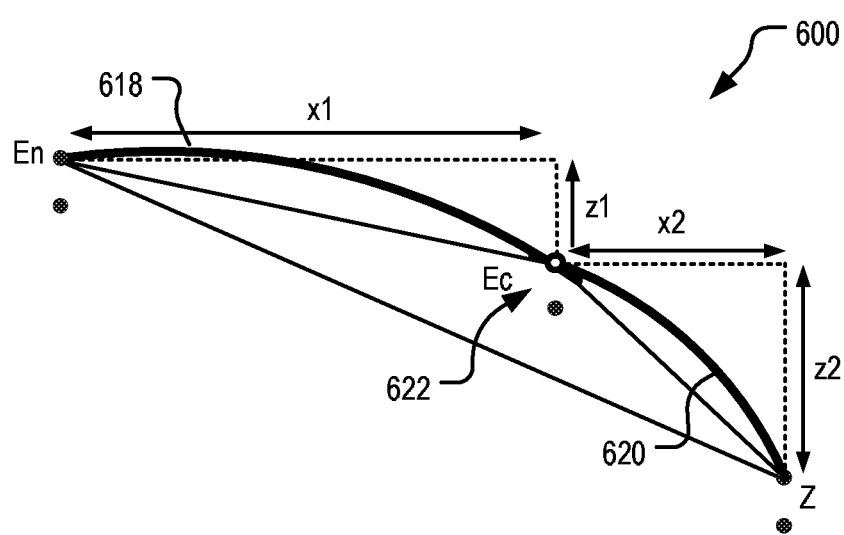
FIG. 6C depicts an example curve fitting process based on the measured location and/or relationship values shown in FIG. 6B.

With reference now to FIG. 6C, a curve 618, with a circular curvature closely matching the horizontal and vertical measures x1 and z1, is chosen.

Although in this example a circular curve has been fitted, it is to be appreciated that non-circular shapes may also be fitted, for example a shape that has a varying value of curvature along its length.

A second curve 620 with a circular curvature (or other shape as defined above) closely matching the horizontal and vertical measures x2 and z2 is also chosen.

The two chosen curves 618, 620 are then extended to their corresponding spherical surfaces. Although, in this example, the two chosen curves 618, 620 are extended to their corresponding spherical surfaces, it is to be appreciated that the extension need not provide a spherical surface. For example, the extension may also provide a toroidal, elliptical, parabolic or hyperbolic shape. In addition, the extension could provide a rotationally symmetric, or a rotationally asymmetric shape.

In the region 622 where the two surfaces intersect the two surfaces are then mathematically merged to create a continuous smooth surface representing the final shape of the lens. The merging of the two surfaces may include using a weighting function whose value varies with distance from the line of intersection of the two surfaces. Examples of suitable merging functions are described in United States patent application no. 2005/0122470, the contents of which is herein incorporated by reference.

Example 2

Example 1 may be applied to dispense a safety lens having 2 mm gap between the rim of the ophthalmic lens and the wearer's face so as to reduce water ingress from incidental splashing. Such a dispensing process may include:
1. Defining an initial ophthalmic lens design as per example 1.
2. Selecting a rimless frame style.
3. Placing an ophthalmic lens conforming to the initial ophthalmic lens design on the 3D representation of the wearer's face in a desired orientation;
4. Extending the lens diameter to determine the intersection between the ophthalmic lens and the wearers face; and
6. Reducing the lens diameter so that a 2 mm gap is maintained between the lens and the wearers face around the periphery of the lens.

In the above example, we have made reference to the term 'lens diameter'. In using that term, we mean the diameter of a surface shape of the ophthalmic lens in all directions radiating out from the geometric centre of the lens (in other words, 360 degrees around). In this respect, if an ophthalmic lens is positioned in front of the wearer's eyes in a desired 'as worn' position, and the lens curved surfaces are extended in all directions, the curved surfaces will make contact with the wearer's face. However, if the curved surfaces do not make contact, the 'curve' of the curved surfaces could be adjusted so that they do.

Figure 7:
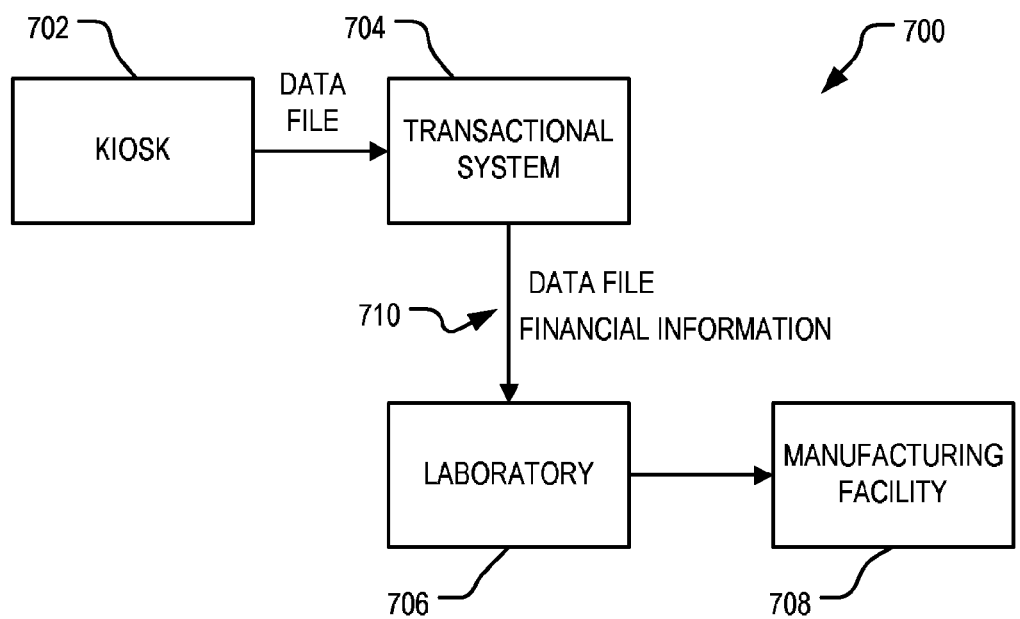
FIG. 7 depicts a block diagram of a dispensing system in accordance with an embodiment of the present invention.

FIG. 7 shows a block diagram for an integrated dispensing system 700. As shown, the system 700 includes a kiosk 702 for gathering the wearer's 3D scan data and recording the wearer's usage/design requirements. The kiosk 702 thus includes a 3D volumetric scanning system of the type described in relation to FIG. 3, and a data processing means for processing the scan data and the usage/design requirements to automatically create a data file containing 3D customer head scan data (or a summary of cardinal points) and information about lens usage or aesthetic requirements. In a typical application, the kiosk 702 may be located at a retail outlet accessible to potential purchase of ophthalmic lens products.

A transactional system 704, in communication with the kiosk 702, receives the data file from the kiosk 700, possibly together with financial information for the wearer (such as credit card information) which may have been entered into the kiosk, and communicates the data file and the financial information from retail outlet to a lens laboratory 706 or designer via a suitable communications channel 710.

At the laboratory 706, design software processes the data file based on one or more measurement values expressing the location of, and/or relationship between selected anatomical features of the wearer's face or head and may also allows an operator to manipulate the data so as to achieve the desired ophthalmic lens type based on the use and aesthetic requirements.

Optionally, the design software then refines the optics of the designed lens to achieve corrected optics after an initial lens shape has been defined. The resultant design file is then communicated to a manufacturing facility 708 for cutting and polishing the ophthalmic lens from a lens blank.

The present invention departs from traditional approaches for spectacle dispensing in that, rather than selecting an ophthalmic lens after having selected a spectacle frame, an embodiment of the present invention is able to dispense an ophthalmic lens for fitting (or attaching) to a frame that is selected subsequently. Because the present invention is able to dispense an ophthalmic lens prior to the selection of a suitable spectacle frame, the spectacle frame may require customisation in order to receive the dispensed ophthalmic lens, particularly for an ophthalmic lens that has an unusual or complex shape.

One technique for designing customised frames to receive an ophthalmic lens having an unusual or complex shape is disclosed in published international patent application WO00/23021A1, the entire contents of which is incorporated herein by reference for the purpose of describing an exemplary method for designing a spectacle frame for receiving unusual or complex shaped ophthalmic lenses.

In conclusion, it must be appreciated that there may be other various and modifications to the configurations described herein which are also within the scope of the present invention.

The invention claimed is:

1. A method of dispensing an ophthalmic lens for a wearer, the method including:
measuring the relative location of, and/or relationship between, selected anatomical features of a wearer's head or face to obtain one or more measurement values for generating a contour map representing a frontal aspect of the wearer's head or the wearer's face;
processing the one or more measurement values to design and/or select an ophthalmic lens having a shape, wherein the shape is a three-dimensional optical surface shape, that depends on the measured values to substantially conform with the contour map, wherein the measurement values are matched to appropriate features of the shape of the ophthalmic lens; and dispensing the ophthalmic lens to the wearer.

2. A method according to claim 1 wherein the shape of the ophthalmic lens substantially conforms to contours of head or facial features of the wearer.

3. A method according to claim 1 wherein the anatomical features of the wearer's head or face are selected to provide measurement values that approximate a contour of a frontal aspect of the wearer's head or face.

4. A method according to claim 3 wherein the contour lies in a substantially vertical plane intersecting the selected anatomical features.

5. A method according to claim 3 wherein the contour lies in a substantially horizontal plane intersecting the selected anatomical features.

6. A method according to claim 1 wherein the shape is a front surface shape of the ophthalmic lens.

7. A method according to claim 1 wherein the ophthalmic lens includes a front surface having a surface shape that depends on the measurement values for the relative location of, and/or the relationship between, selected anatomical features of a wearer's head and/or face, and a back surface includes a central zone having a surface shape that corrects optical aberrations introduced by the front surface shape.

8. A method according to claim 1 wherein measuring the location of, and/or relationship between, the selected anatomical features of the wearer's head or face to obtain one or more measurement values includes:

obtaining scan data derived from a three-dimensional scan of the wearer's head or face; and processing the scan data to obtain a measurement value for each of the selected anatomical features.

9. A method according to claim 1 wherein the anatomical features of the wearer's head are selected from the zygion, the zygomatic arch, the frontal eminence, the temporomandibular joint and the mandible angle.

10. A method according to claim 1 wherein the anatomical features of the wearer's face include anatomical features of the wearer's eye and/or eyelids.

11. A method according to claim 10 wherein the anatomical features of the wearer's eye and/or eyelids are selected from the pupil, the medial angle, the lateral angle, the medial commissure, the lateral commissure, the medial canthus, the lateral canthus, the lacarimal caruncle, the nasojugal fold, the lower eyelid margin, and the palperal fissure.

12. A method according to claim 1 wherein selecting an ophthalmic lens having a surface shape that depends on the measured values includes selecting an ophthalmic lens from an array of ophthalmic lenses having a predefined relationship with a range of values for the anatomical features.

13. A method according to any one of claim 1 wherein designing an ophthalmic lens having a shape that depends on the measured values includes defining a surface geometry based on the measured values.

14. A method according to claim 1 wherein designing an ophthalmic lens having a surface shape depending on the measured values includes designing an ophthalmic lens having a single base curve that depends on the measured values.

15. A method according to claim 1 further including modifying the surface shape of the designed ophthalmic lens according to blur and/or prism conditions.

16. A method according to claim 15 wherein modification of the surface shape of the designed ophthalmic lens minimizes blur across a central viewing zone of the ophthalmic lens while controlling ray-traced prism in peripheral areas of the lens.

17. A method according to claim 1 wherein the method further includes querying the wearer to obtain wearer information describing the intended purpose and/or functional requirements of the ophthalmic lens, and processing that information, together with the measurement values, to dispense an ophthalmic lens having a surface shape that depends on the measured values and the wearer information.

18. A method according to claim 17 wherein processing the wearer information and the measurement values dispenses an ophthalmic lens having a parameter that has been optimized within the constraints of the measured values, the optimized parameter being associated with the intended purpose and/or function of the ophthalmic lens.

19. A method according to claim 18 wherein the optimized parameter is selected from a group consisting of:
 a. aerodynamic coefficient of drag;
 b. splash protection;
 c. glare protection; and
 d. field of view.

20. A method according to claim 19 wherein the optimized parameters are optimized for a specific application of the ophthalmic lenses.

21. A system for dispensing an ophthalmic lens for a wearer, the system including:

a measuring apparatus for measuring the relative location of, and/or relationship between, selected anatomical features of a wearer's head or face to obtain one or more measurement values for generating an approximation of a contour map representing a frontal aspect of the wearer's head or the wearer's face; and a processing device for processing the one or more measurement values to dispense the ophthalmic lens, the dispensing including selecting or designing an ophthalmic lens having a shape, wherein the shape is a three-dimensional optical surface shape, that depends on the one or more measured values to substantially conform with the contour map, wherein the measurement values are matched to appropriate features of shape of the ophthalmic lens.

22. A system according to claim 21 wherein measuring apparatus includes a three dimensional scanning device for providing a three-dimensional scan for the wearer's head or face.

23. A system according to claim 21 further including a database storing an array of ophthalmic lenses having a predefined relationship with a range of values for the anatomical features.

24. A programmed computer for dispensing an ophthalmic lens for dispensing to a wearer, the computer including:
 a processing device;
 a memory; and
 a set of program instructions resident in the memory and executable by the processor to accept one or more measurement values expressing the relative location of, and/or the relationship between, selected anatomical features of a wearer's head or face for generating an approximation of a contour map representing a frontal aspect of the wearer's head or the wearer's face and to process the measurement values to design and/or select an ophthalmic lens for dispensing, the ophthalmic lens having a shape, wherein the shape is a three-dimensional optical surface shape, that depends on the measured values to substantially conform with the contour map, wherein the measurement values are matched to appropriate features of the three-dimensional optical surface shape of the ophthalmic lens.

25. An integrated scanning and processing system for selecting and/or designing an ophthalmic lens for dispensing to a wearer, the system including:
  a scanning device for scanning the wearer's head or face to provide three-dimensional scan data;
  an input device for inputting or selecting anatomical features of the wearer's face or head; and
  a processing device for obtaining, from the three-dimensional scan data, one or more measurement values expressing the relative location of, and/or the relationship between, the anatomical features and to process the measurement values to design and/or select an ophthalmic lens for dispensing, the ophthalmic lens having a shape, wherein the shape is a three-dimensional optical surface shape, that depends on the measured values, wherein the measurement values are matched to appropriate features of the shape of the ophthalmic lens.

26. A computer readable media storing a set of program instructions that are executable by a computer processor to accept one or more measurement values expressing the relative location of, and/or the relationship between, selected anatomical features of a wearer's head or face for generating an approximation of a contour map representing a frontal aspect of the wearer's head or the wearer's face; and to process the one or more measurement values to select and/or design, for dispensing, an ophthalmic lens having a shape, wherein the shape is a three-dimensional optical surface shape, that depends on the measured values to substantially conform with the contour map, wherein the measurement values are matched to appropriate features of the shape of the ophthalmic lens.

27. A method according to claim 1 wherein the selected anatomical features of a wearer's head or face include at least one of an endocanthus or ectocanthus.

28. A method according to claim 1 comprising reducing a lens diameter so that an approximately 2 mm gap would be maintained between the lens and a wearer's face around the periphery of the lens.

29. A method according to claim 1 wherein processing the one or more measurement values to design and/or select an ophthalmic lens having a three-dimensional optical surface shape that depends on the measured values to substantially conform with the contour map includes designing one surface of the lens for aesthetic purposes and an optimizing second optical surface of the lens to correct prescription and off-axis optics over a substantial portion of the lens surface.

30. A system according to claim 21 wherein processing the one or more measurement values to design and/or select an ophthalmic lens having a three-dimensional optical surface shape that depends on the measured values to substantially conform with the contour map includes designing one surface of the lens for aesthetic purposes and an optimizing second optical surface of the lens to correct prescription and off-axis optics over a substantial portion of the lens surface.

31. A programmed computer according to claim 24 wherein processing the one or more measurement values to design and/or select an ophthalmic lens having a three-dimensional optical surface shape that depends on the measured values to substantially conform with the contour map includes designing one surface of the lens for aesthetic purposes and an optimizing second optical surface of the lens to correct prescription and off-axis optics over a substantial portion of the lens surface.

32. An integrated scanning and processing system according to claim 25 wherein processing the one or more measurement values to design and/or select an ophthalmic lens having a three-dimensional optical surface shape that depends on the measured values to substantially conform with the contour map includes designing one surface of the lens for aesthetic purposes and an optimizing second optical surface of the lens to correct prescription and off-axis optics over a substantial portion of the lens surface.

* * * * *